United States Patent [19]

Barone et al.

[11] Patent Number: 6,036,947

[45] Date of Patent: *Mar. 14, 2000

[54] TRANSFER RESISTANT HIGH LUSTRE LIPSTICK COMPOSITIONS

[75] Inventors: Salvatore Joseph Barone, Staten Island, N.Y.; Ann Marshall Krog, Red Bank, N.J.; Natividad Jose, Jamaica, N.Y.; Renee Joan Ordino, Edison, N.J.

[73] Assignee: Revlon Consumer Products Corporation, New York, N.Y.

[*] Notice: This patent is subject to a terminal disclaimer.

[21] Appl. No.: 09/196,615

[22] Filed: Oct. 23, 1998

Related U.S. Application Data

[63] Continuation of application No. 08/689,588, Aug. 12, 1996, Pat. No. 5,837,223.

[51] Int. Cl.$^7$ ..................................................... A61K 7/027

[52] U.S. Cl. .......................... 424/64; 424/78.02; 424/401; 424/DIG. 5

[58] Field of Search ..................................... 424/64, 78.02, 424/49, DIG. 5

[56] References Cited

U.S. PATENT DOCUMENTS 5,800,816  9/1998  Brieva et al. ............................. 424/63
5,837,223  11/1998  Barone et al. ............................ 424/64

*Primary Examiner*—Jyothsna Venkat
*Attorney, Agent, or Firm*—Julie Blackburn

[57] ABSTRACT

An anhydrous cosmetic stick composition with improved transfer resistance and luster finish comprising, by weight of the total composition:

a) 10–70% of a volatile solvent having a viscosity of 0.5 to 20 centipoise at 25° C.,
b) 0.5–40% of a guerbet ester, and
c) 0.1–20% of a siloxysilicate polymer.

6 Claims, No Drawings

TRANSFER RESISTANT HIGH LUSTRE LIPSTICK COMPOSITIONS

This is a continuation of application Ser. No. 08/689,588, filed Aug, 12, 1996 now a U.S. Pat. No. 5,837,223.

TECHNICAL FIELD

The invention is in the field of cosmetic compositions for application to skin and lips.

BACKGROUND OF THE INVENTION

Cosmetic compositions are generally defined as compositions suitable for application to the human body. Pigmented cosmetic compositions such as makeup, blush, lipstick, and eyeshadow are used to color the skin and lips, or to moisturize, hide wrinkles, and the like. Since color is one of the most important reasons for wearing cosmetics, color containing cosmetics must be very carefully formulated to provide maximum wear and effect One of the long standing problems with makeups such as face makeup, lipstick, mascara, and the like, is the tendency of the cosmetic to blot or transfer from the skin or lashes onto other surfaces such as glassware, silverware, skin, or clothing. This not only creates soiling, but forces the cosmetic user to reapply the cosmetic at fairly short intervals.

Cosmetic compositions with improved transfer resistance are disclosed in U.S. Pat. No. 5,505,937 which is hereby incorporated by reference. However, these transfer resistant cosmetic compositions can have a matte texture on the skin and lips.

However, some consumers prefer lipsticks that exhibit a lustre finish on the lips. The term "lustre" means that the finish is mid-way between shiny and matte, exhibiting slightly more shine than what is provided by a semi-matte finish. Some consumers believe that very shiny lipsticks provide a very youthful look which is not appropriate on older women. On the other hand, such consumers are not pleased with a completely matte finish. Lipsticks which provide a lustre finish will provide a degree of shine which provides a dewy look associated with youth and good health, but not so shiny as to be patently obvious.

In general, the ingredients that can be added to provide lustre have a tendency to compromise transfer resistance.

It has been unexpectedly discovered that cosmetic compositions containing the combination of a volatile solvent, a guerbet ester, and siloxy silicate polymer provide a high lustre lipstick composition which exhibits transfer resistance which is equivalent if not better than the traditional matte formulas.

An object of this invention is to formulate cosmetic compositions, particularly lipsticks, with long lasting adherence to skin that provide a lustre finish when applied to skin.

Another object of this invention is to formulate a transfer resistant cosmetic composition that provides a lustre finish, that, once applied to skin, resists transfer to glass, clothing, other skin, or utensils.

SUMMARY OF THE INVENTION

The invention is directed to high lustre, transfer resistant anhydrous cosmetic stick composition comprising, by weight of the total composition:

a) 10–70% of a volatile solvent having a viscosity of 0.5 to 25 centistokes at 25° C.,
b) 0.5–40% of a guerbet ester
c) 0.1–20% siloxy silicate polymer.

The invention is also directed to a method for providing a cosmetic stick composition with transfer resistance and a high lustre finish when applied to skin, comprising adding to said composition the combination of a volatile solvent, a guerbet citrate ester, and trimethylsiloxy silicate.

DETAILED DESCRIPTION

The term "stick" refers to cosmetic compositions having a consistency such that they can be molded into the form of a stick—for instance by being heated until molten and then poured into a mold and cooled. Also included within the definition of "stick" are anhydrous compositions of the invention that are capable of being formed into sticks, but are poured into pans or other types of cake or cream forms to deliver certain consumer benefits. For example, an eyeshadow composition in accordance with the invention may be molded in the stick form, but it may be desired to pour it into a pan because this container is more desireable from a consumer standpoint. The term "anhydrous" means that the composition contains no more than about 5 percent, more particularly about 1 to 2 percent by weight or less of water, or more preferably, that water is not intentionally added to the cosmetic composition of the invention. All percentages mentioned herein are percentages by weight unless otherwise indicated.

THE VOLATILE SOLVENT

The composition of the invention contains 10–70%, preferably 15–60%, more preferably 20–60% of a volatile solvent The volatile solvent component of the composition is a liquid, and enables easy formulation of the cosmetic stick of the invention. The term "volatile" means that the solvent has a measureable vapor pressure, i.e. a vapor pressure of at least 2 mm. of mercury at 20° C. When the cosmetic stick product of the invention is applied to skin or lips, the volatile solvent of the invention must be capable of flashing off to leave the other ingredients in the stick on the skin. The composition of the invention comprises 10–70%, preferably 20–65%, and most preferably 25–60% of a volatile solvent. The volatile solvent generally has a viscosity of 0.5 to 25 centistokes at 25° C. Suitable volatile solvents include linear silicones, cyclic silicones, paraffinic hydrocarbons, or mixtures thereof.

Cyclic silicones (or cyclomethicones) are of the general formula:

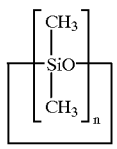

where n=3–7.

Linear volatile silicones in accordance with the invention have the general formula:

where n=0–7, preferably 0–5.

Linear and cyclic volatile silicones are available from various commercial sources including Dow Corning Corporation and General Electric. The Dow Corning volatile silicones are sold under the tradenames Dow Coming 244, 245, 344, and 200 fluids. These fluids comprise octamethylcyclotetrasiloxane, decamethylcyclopentasiloxane, hexamethyldisiloxane, and mixtures thereof.

Also suitable as the volatile solvent are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular eight of 70–190, preferably 160 to 180 and a boiling point range of 30 to 320, preferably 60–260 degrees C., and a viscosity of less than 20 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. The volatile

THE GUERBET ESTER

The composition of the invention contains 0.5–40%, preferably 1–30%, more preferably 2–20% of a guerbet ester. The term "guerbet ester" means an ester which is formed by the reaction of a guerbet alcohol having the general formula:

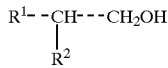

with a carboxylic acid having the general formula:

$R^3COOH$, or $HOOC—R^3—COOH$ wherein $R^1$ and $R^2$ are each independently a $C_{4-20}$ alkyl and $R^3$ is a substituted or unsubstituted $C_{1-50}$ straight or branched chain saturated alkyl or alkylene, or phenyl, wherein the substituents are halogen, hydroxyl, carboxyl, and alkylcarbonylhydroxy.

Preferably, the guerbet ester is a fluoro-guerbet ester which is formed by the reaction of a guerbet alcohol and carboxylic acid (as defined above), and a fluoroalcohol having the following general formula:

$CF_3—(CF_2)_n—CH_2—CH_2—OH$ wherein n is from 3 to 40.

Examples of guerbet esters are as set forth in U.S. Pat. No. 5,488,121 which is hereby incorporated by reference. Suitable fluoro-guerbet esters are set forth in U.S. Pat. No. 5,312,968 which is hereby incorporated by reference.

Most preferred is a guerbet ester having the tentative CTFA name fluoro-octyldodecyl meadowfoamate. This ester is sold by Siltech, Norcross Ga. as Developmental Ester L61125A, under the tradename Silube GME-F.

THE SILOXY SILICATE POLYMER

The composition comprises 0.1–20%, preferably 0.5–15%, more preferably 1–12% of a siloxy silicate polymer having the following general formula:

wherein R, R' and R" are each independently a $C_{1-10}$ straight or branched chain alkyl or phenyl, and x and y are such that the ratio of $(RR'R")_3SiO_{1/2}$ units to $SiO_2$ units is 0.5 to 1 to 1.5 to 1.

Preferably R, R' and R" are a $C_{1-6}$ allyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which-are hereby incorporated by reference. Trimethylsiloxy silicate as described is available from Dow Coming Corporation under the tradename 2-0749 and 2-0747, which is a blend of about 40–60% volatile silicone and 40–60% trimethylsiloxy silicate. Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

OTHER INGREDIENTS

Waxes

The cosmetic compositions of the invention generally contain from about 1–40%, preferably 1–30%, more preferably 2–25% by weight of a cosmetically acceptable natural or synthetic wax. An acceptable wax can be a solid or semi-solid wax having a melting point of 30 to 120° C. and generally includes animal waxes, plant waxes, mineral waxes, silicone waxes, synthetic waxes, and petroleum waxes. Examples of waxes in accordance with the invention include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEGS beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, polyethylene, stearoxy dimethicone, dimethicone behenate, stearyl dimethicone, and the like, as well synthetic homo- and copolymer waxes such as PVP/eicosene copolymer, PVP/hexadecene copolymer, and the like.

Oils

The cosmetic compositions of the invention may also contain about 0. 1–30, preferably 0.5–25, more preferably 1–20% by weight of a cosmetically acceptable oil. The oils are nonvolatile, which means that they do not have a measureable vapor pressure, i.e. have a vapor pressure of less than about 2 mm. mercury at 20° C. Preferably, the nonvolatile oil has a viscosity ranging from 10 to 1,000,000 centipoise at 25° C., preferably 20 to 600,000 centipoise at 25° C.

The oil may comprise esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEGA4 diheptanoate, isostearyl neopentanoate, tridecyl neopentanoate, cetyl octanoate, cetyl palmitate, cetyl ricinoleate, cetyl stearate, cetyl myristate, coco-dicaprylate/ caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the *C.T.F.A. Cosmetic Ingredient Handbook* First Edition, 1988, which is hereby incorporated by reference.

The oil may also comprise glyceryl esters of1fatty acids, or triglycerides, such as castor oil lanolin oil, triisocetyl citrate, $C_{10-18}$ triglycerides, caprylic/capric/triglycerides, coconut oil, corn oil cottonseed oil, linseed oil mink oil, olive oil, palm oil, illipe butter, rapeseed oil, soybean oil sunflower seed oil, walnut oil, and the like.

Also suitable as the oil are glyceryl esters (excluding fats and oils which are glyceryl esters of fatty acids) which are primarily fatty acid mono-di- and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Nonvolatile nonfluorinated silicones are also suitable as the oil component Such silicones preferably have a viscosity of 10 to 600,000 centistokes, preferably 20 to 100,000 centistokes at 25° C. Suitable silicones include amodimethicone, bisphenylhexamethicone, dimethicone, dimethicone copolyol, dimethiconol, hexadecyl methicone, hexamethyldisiloxane, methicone, phenyl trimethicone, simethicone, dimethylhydrogensiloxane, stearoxy dimethicone, stearoxytrimethylsilane, vinyldimethicone, and mixtures thereof. Such silicones are available from Dow Corning as the 3225C formulation aid, Dow 190 and 193 fluids, or similar products marketed by Goldschmidt under the ABIL tradename.

Also suitable as the oil are various fluorinated oils such as fluorinated silicones or perfluoropolyether. Particularly suitable are fluorosilicones such as trimethylsilyl endcapped fluorosilicone oil polytrifluoropropylmethylsiloxanes, and similar silicones such as those disclosed in U.S. Pat. No. 5,118,496 which is hereby incorporated by reference. The nonvolatile component may comprise mixtures of fluorosilicones and dimethylpolysiloxanes. The nonvolatile component may also comprise perfluoropolyethers like those disclosed in U.S. Pat. Nos. 5,183,589, 4,803,067, 5,183,588 all of which are hereby incorporated by reference. These perfluoropolyethers are commercially available from Montefluos under the trademark Fomblin Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

Pigments and Powders

The composition of the invention may contain 5–50%, preferably 7–45%, more preferably 10–40%, by weight of the total composition, of dry particulate matter having a particle size of 0.02 to 200, preferably 0.5 to 100, microns. The particulate matter may be colored or non-colored (for example white). Suitable powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof The above mentioned powders may be surface treated with lecithin, amino acids, mineral oil, silicone oil or various other agents either alone or in combination, which coat the powder surface and render the particles more lipophilic in nature.

The powder component also may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof Preferably the composition will contain both pigment and non-pigmented powders. Obviously the percentage of pigments used in the powder component will depend on the type of cosmetic being formulated. Color cosmetics generally have a much higher concentration of color than other types of cosmetics. Generally the weight ratio of pigment to non-pigmented powder will range from 1:20 to 20:1.

Preferred anhydrous stick cosmetic compositions in accordance with the invention comprise, by weight percent:

a) 10–70% of a volatile solvent,
b) 0.1–40% of a guerbet ester,
c) 0.1–20% siloxy silicate polymer
d) 1–40% of a wax having a melting point of 30 to 120° C.,
e) 0.1–30% oil, and
f) 5–50% dry particulate matter.

A more preferred embodiment of the invention comprises anhydrous lipstick compositions comprising, by weight percent:

a) 10–70% cyclomethicone,
b) 0.5–20% fluoro guerbet ester,
c) 0.1–40% of a wax having a melting point of 30 to 120° C.,
d) 0.1–30% oil,and
e) 5–50% of a dry particulate matter that comprises pigments, powders, or mixtures thereof, having a particle size of 0.02 to 100 microns.

The invention will be further described in connection with the following examples which are set forth for the purpose of illustration only.

EXAMPLE 1

A transfer resistant lipstick with lustre finish was made as follows:

|  | w/w % | |
|---|---|---|
| Fluoro-octyldodecyl meadowfoamate* | 6.00 | 6.00 |
| Diisodecyl adipate | 3.00 | 3.00 |
| Synthetic wax | 8.00 | 8.00 |
| Polywax 500 (polyethylene wax) | 2.50 | 2.50 |
| Vitamin E acetate | 0.10 | 0.10 |
| Apple extract/hydrogenated vegetable oil | 0.30 | 0.30 |
| Aloe extract | 1.00 | 1.00 |
| Propyl paraben | 0.10 | 0.10 |
| Butylated hydroxy anisole (BHA) | 0.10 | 0.10 |
| Pigment grind** | 11.00 | 11.00 |
| Mica/silica | 13.80 | 13.80 |
| Mica/nylon | 5.00 | 5.00 |
| Mica | 2.10 | 2.10 |
| Isododecane | 9.50 | 9.00 |
| PVP/Eicosene copolymer | 5.00 | 5.00 |
| Lanolin oil | 5.00 | 5.00 |
| Cyclomethicone/trimethylsiloxysilicate (50:50) | 5.00 | 10.00 |
| Cyclomethicone | 27.50 | 17.00 |

*Silube GME-F, Developmental Ester L61125A - Siltech, Norcross Georgia
**D&C Red #7 Calcium Lake and lanolin oil The liquid ingredients, other than the cyclomethicone, were mixed. The pigments and other powders were added. The wax materials were combined and heated to a molten mass, and then added to the liquid material with mixing. After complete mixing, the molten mass was poured into the desired containers and allowed to cool. The lipstick provided a lustre finish to the lips when applied and was transfer resistant.

We claim:

1. An anhydrous lipstick composition with improved transfer resistance and lustre finish comprising, by weight of the total composition:

a) 10–70% cyclomethicone,
   b) 0.5–40% of a guerbet ester, and
   c) 0.1–20% trimethylsiloxysilicate which is the reaction product of the sodium salt of silicic acid, chlorotrimethylsilane, and isopropyl alcohol,
   d) 0.1–30% of a nonvolatile silicone oil,
   e) 1–40% silicone wax; and
   f) 5–50% dry particulate matter.

2. The composition of claim 1 wherein the wax is a solid or semi-solid having a melting point of 30 to 120° C.

3. The composition of claim 2 wherein the wax comprises stearyl dimethicone.

4. The composition of claim 1 wherein the nonvolatile silicone oil has a viscosity of 10 to 600,000 centistokes at 25° C.

5. The composition of claim 1 wherein the silicone oil is a fluorinated silicone.

6. The composition of claim 5 wherein the fluorinated silicone is polytrifluoropropylmethylsiloxane.

* * * * *